United States Patent [19]

Scott et al.

[11] 4,158,738

[45] Jun. 19, 1979

[54] PROCESS FOR THE PRODUCTION OF FIBER-GRADE TEREPHTHALIC ACID

[75] Inventors: Leon S. Scott, Wilmington, Del.; Roy W. Sommers, Pennsville, N.J.

[73] Assignee: E. I. Du Pont de Nemours and Company, Wilmington, Del.

[21] Appl. No.: 800,868

[22] Filed: May 26, 1977

[51] Int. Cl.² ............................................. C07C 51/42
[52] U.S. Cl. .................................... 562/416; 562/414
[58] Field of Search ................... 260/524 R; 562/416, 562/414

[56] References Cited

U.S. PATENT DOCUMENTS

| | | | |
|---|---|---|---|
| 2,890,245 | 6/1959 | Bonnet | 260/524 R |
| 3,089,906 | 5/1963 | Saffer | 260/524 R |
| 3,092,658 | 6/1963 | Baldwin | 260/524 R |
| 3,920,735 | 11/1975 | Wampfler | 280/524 R |

Primary Examiner—A. Siegel

[57] ABSTRACT

Process for the preparation of fiber-grade terephthalic acid by continuously oxidizing paraxylene while vaporizing a portion of the contents of the reactor. Fiber-grade terephthalic acid is produced by maintaining (1) a temperature of at least 210° C., (2) a molecular oxygen content of the noncondensables in the vapor withdrawn from the reactor in the range 3.0–6.0%, (3) a water level of the contents of the oxidizer in the range 5.0–17.0%, (4) a mole ratio of sodium to cobalt plus manganese in the range 0.06–2.0 in the reactor, (5) a mole ratio of cobalt to manganese in the range 0.5–5.0 (6) an organic burn in the range 8.0–15.0 burn units and (7) a productivity in the range 0.45–1.45 pounds of terephthalic acid per minute per 100 pounds of reactor contents.

10 Claims, 4 Drawing Figures

FIG. III

FIG. IV

PROCESS FOR THE PRODUCTION OF FIBER-GRADE TEREPHTHALIC ACID

BACKGROUND OF THE INVENTION

1. Field of the Invention

The present invention relates to a process for the preparation of terephthalic acid by the liquid phase oxidation of paraxylene. More particularly, the present invention relates to the production of terephthalic acid at high productivity which acid is of sufficient purity so that it can be directly polymerized with ethylene glycol to form polyester without complicated and/or expensive purification.

2. Description of the Prior Art

There is a recognized economic benefit in continuously producing terephthalic acid of sufficient purity so that the acid can be directly polymerized with ethylene glycol after relatively simple methods of separation and purification. Various modifications to the known procedures for the oxidation of paraxylene to produce such fiber-grade terephthalic acid have been proposed. These include changing oxidation conditions, catalysts levels and composition, and recovery of terephthalic acid. However, the modifications are frequently in conflict. British Pat. No. 1,249,198 published on Oct. 6, 1971 describes a process which allegedly produces terephthalic acid of high purity and reduced color by conducting the oxidation at a maximum temperature of 200° C. using specified amounts of manganese, bromine and a specified atomic ratio of cobalt to manganese. British Pat. No. 983,677 published on Feb. 17, 1965 describes the production of terephthalic acid of enhanced purity by two stage oxidation with the second stage using gaseous molecular oxygen at temperatures higher than those employed in the first stage and usually above 200° C. and preferably 230° to 280° C. The use of air diluted with an inert gas (5 to 17 volume percent oxygen) is alleged to produce high purity terephthalic acid in unexamined Japanese Patent Application No. 50-30839 published on Mar. 27, 1975. A number of catalysts have also been proposed. U.S. Pat. No. 3,846,487 issued on Nov. 5, 1974 alleges beneficial results by using cobalt bromide and free bromine ($Br_2$) exclusively as the source of bromide whereas bromoform as the sole source of bromine is alleged to have a beneficial effect in unexamined Japanese Patent Application 51-43734 published on Apr. 14, 1976. Although alkali metal ions, e.g., sodium are taught to be beneficial in U.S. Pat. No. 2,959,613 issued on November 8, 1960, the presence of such ions are taught to be detrimental to the production of relatively pure terephthalic acid in U.S. Pat. No. 3,970,696 issued on July 20, 1976. The use of hydrogen bromide as a source of bromine along with an alkali metal is taught to produce high purity terephthalic acid in Japanese Pat. Application 51-70741 published on June 18, 1976. Mole ratios of cobalt to manganese of at least about 4.7 up to 91 are taught to be beneficial for producing terephthalic acid of high purity in unexamined Japanese Patent Application 45-36732 published on Nov. 21, 1970.

German Pat. No. 2,534,161 opened for inspection on Feb. 12, 1976 teaches that maintenance of 4-carboxybenzaldehyde in the mother liquor of the terephthalic acid slurry in the oxidation vessel at less than 800 parts per million provides a high quality terephthalic acid.

Certain mechanical arrangements are also taught to be beneficial to the production of highly pure terephthalic acid. U.S. Pat. No. 3,839,435 issued on Oct. 1, 1974 discloses introducing paraxylene in at least three inlets distributed at differing heights in the vertical plane of the reaction vessel. Unexamined Japanese Patent Application 47-14092 published on Apr. 27, 1972 teaches introducing paraxylene into the reactor by passing it through a hollow stirring shaft with a multiple number of hollow stirring blades so that the paraxylene is fed through the openings of the rotating stirring blades and thereby is more thoroughly dispersed in the reaction medium. Advantages are alleged by adding raw paraxylene to the condensate reflux of the reactor in unexamined Japanese Patent Application 49-20192 published on May 23, 1974.

Post treatment of the oxidate to reduce impurities is also taught to be beneficial. U.S. Pat. No. 3,859,344 issued on Jan. 7, 1975 discloses treating the oxidate with a molecular oxygen containing gas for a short period while the oxidate is intermittently withdrawn from the oxidation reactor. The use of an oxygen containing gas having an oxygen level less than that of air is disclosed to be beneficial in the post oxidative treatment of the oxidate as disclosed in unexamined Japanese Pat. Application 51-39642 published on Apr. 2, 1976. U.S. Pat. No. 3,507,913 issued on Apr. 21, 1970 discloses a technique for recovery of the reaction product from the oxidation by adding one-tenth to five times the volume of the reaction product of acetic acid before the temperature of the product decreases below 180° C. and before the amount of precipated terephthalic acid exceeds 20% by weight based upon the weight of the liquor. The maintenance of a specific temperature during the recovery of terephthalic acid to enhance its purity is disclosed in U.S. Pat. No. 3,996,271 issued on Dec. 7, 1976.

SUMMARY OF THE INVENTION

A process for the preparation of fiber-grade terephthalic acid comprising contacting paraxylene with a molecular oxygen containing gas in a reactor in the presence of a catalyst consisting essentially of cobalt, manganese and bromine and a solvent comprising a lower monocarboxylic acid wherein (1) the reaction is conducted in the liquid phase, (2) a portion of the contents of the reactor is continuously vaporized, condensed, and a portion of the condensate withdrawn from the system and (3) the product is withdrawn and subjected to treatment before the recovery of the terephthalic acid, including the improvement comprising maintaining a high productivity of fibergrade terephthalic acid by maintaining (1) the temperature of the contents of the reactor at at least 210° C., (2) the molecular oxygen content of the vapor withdrawn from the reactor in the range 3.0–6.0% by volume at least in part by controlling the molecular oxygen introduced into the reactor, (3) the water level of the contents of the oxidizer in the range 5.0–17.0% by weight based upon the weight of the liquid portion of the contents of the reactor by controlling the amount of condensate from the reactor which is withdrawn from the system, (4) the mole ratio of sodium to cobalt plus manganese in the range of about 0.06–2.0 in the reactor, (5) a cobalt to manganese mole ratio of 0.5–5.0, (6) the organic burn in the range 8.0–15.0 burn units and (7) the productivity of the reaction in the range of 0.45–1.45 pounds per minute of terephthalic acid, per 100 pounds of reactor content.

DETAILED DESCRIPTION OF THE INVENTION

Figure 1:
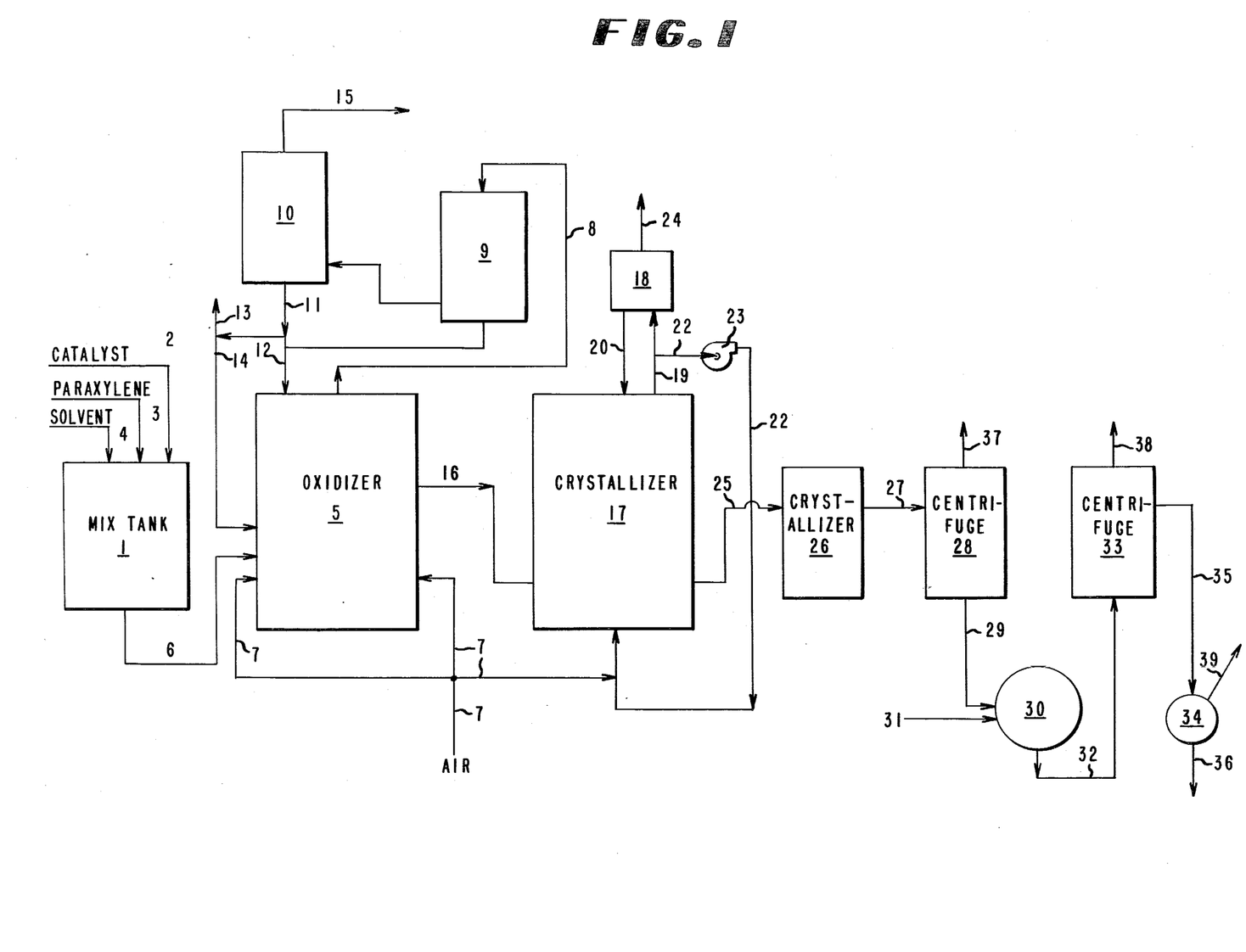
FIGS. 1 and 2 are flow diagrams illustrating the process of the invention.

A more complete understanding of the present invention may be had by referring to FIG. 1 which is a schematic of the apparatus used to practice the process of the present invention. The mixture to be oxidized is prepared by introducing into mix tank 1 catalyst and promoter (line 2), paraxylene (line 3) and solvent (line 4). The catalyst is charged as a solution of cobalt acetate, manganese acetate, hydrogen bromide and sodium bromide in water. The solvent (line 4) can be essentially pure acetic acid or may comprise a portion of recycled acetic acid obtained as hereinafter described. In the latter case the solvent contains less than about 10% and usually 4–6% water based upon the total weight of the stream. The oxidation charge is thoroughly mixed in tank 1 and then directed to oxidizer 5 via line 6 at a point approximately ½ of the vertical distance from the bottom of the oxidizer. Air is introduced into oxidizer 5 via line 7 at two opposite points on the horizontal plane of the oxidizer approximately 1/5 of the vertical distance from the bottom. The off gas from the oxidizer 5 (line 8) is passed through two condensers 9 and 10 arranged in series. A portion of the hot condensate from condenser 9 (line 12) is returned to the upper portion of the agitator mechanism of oxidizer 5 in order to bathe the upper internal portion of the oxidizer. The remaining condensate (line 11) along with the hot condensate from condenser 9 which is not fed to reactor 5 via line 12 is either returned to the oxidizer at approximately 1/5 of the vertical distance from the bottom (line 14) or is removed (line 13) from the system and directed to suitable apparatus for recovery of desirable materials. Vapor is removed via line 15 and directed to recovery or recycle of condensables. The product is removed as a slurry from oxidizer 5 via line 16 and directed to oxidizer/crystallizer 17 to further the oxidation of terephthalic acid precursors and/or the destruction of undesirable impurities. The off gas from crystallizer 17 is directed to condenser 18 via line 19 where most of the condensables are removed and returned to the crystallizer via line 20. A portion of the off gas is withdrawn from line 19 via line 22 and directed to pump 23 which pressurizes the gas to permit its return to the crystallizer along with makeup air (line 7) to maintain a preset oxygen level in the off gas stream 24. The slurry from the crystallizer/oxidizer 17 (line 25) is then passed through two additional crystallizers 26 connected in series where the product is cooled to about 105° C. following which cooled slurry is directed via line 27 to centrifuge 28. The centrifuge cake (line 29) is then reslurried in tank 30 with fresh acetic acid introduced via line 31. After reslurrying, the slurry (line 32) is then directed to centrifuge 33 and thence to drier 34 via line 35 where the product (line 36) is recovered. The liquid discharge from centrifuges 28 and 33 and the vapor discharge from drier 34 (lines 37, 38 and 39, respectively), are directed to suitable recovery apparatus.

As used herein, the term "fiber-grade terephthalic acid" means terephthalic acid of at least 99.8% purity on a dry basis. Such acid must also contain less than 775 parts per million paraformylbenzoic acid (PFBA) and less than 20 and preferably less than 15 parts per million 2,6-dicarboxyfluorenone (DCF), since both of these impurities adversely affect the color of the acid and the polymer made therefrom.

The color of the terephthalic acid is referred to herein as TPA "b" color and must be less than 2.0 in commercial equipment in order for the acid to produce polymer which has acceptable color. TBA "b" color is determined on dry acid by measuring the color using a Hunter Lab ® D-25 Color Difference Meter against a standard white reference. Acid having less than the maximum TBA "b" specified hereinabove will, under normal conditions, i.e., in the absence of unusual color-forming contaminants produce satisfactory polymer.

The present invention comprises operating the oxidation under a novel set of conditions which provides sufficiently pure terephthalic acid at acceptable rates with the desired consumption of acetic acid.

Applicants have discovered that it is necessary to burn a certain amount of acetic acid during the oxidation in order to produce terephthalic acid of acceptable purity and that a certain productivity must be maintained to achieve commercially acceptable rates. Excessive burn and low productivity make the process uneconomic. The desired conditions to achieve a satisfactory range of burn and productivity cannot be identified by the usual method of listing ranges of operation but require a detailed specification of the interaction of those parameters. A discussion of the conditions which must be employed for satisfactory operation and the further constraint on the conditions within the general range which must be selected is set forth hereinbelow.

The oxidation temperature must be maintained at at least 210° C., usually in the range 210°–250° C. and preferably in the range 215°–223° C. Oxidations at temperatures below 210° C. require a higher catalyst level for an equivalent purity and productivity, e.g., approximately four times higher catalyst levels are required at an oxidation temperature of 190° C. for a burn and productivity equivalent to operation at 220° C. Lower temperature operation results in higher catalyst costs or necessitates costly catalyst recovery facilities. Either situation is an economic penalty relative to the higher temperature oxidation. Operation at higher temperatures also improves energy (heat) recovery with the associated economic benefits. The pressure at which the oxidation is conducted is adjusted to be sufficient to prevent excessive vaporization of the oxidation mixture, to control the amount of vapor from the oxidation and to control the temperature of the oxidation.

As discussed hereinabove, the catalyst employed in the present oxidation can include soluble species of metallic ions in addition to cobalt and manganese but their presence is not preferred. The catalyst is preferably introduced as an aqueous solution of cobalt and manganese acetate, hydrogen bromide and sodium bromide in water. The relative amount of cobalt and manganese is an essential consideration for the present invention. The cobalt/manganese mole ratio (Co/Mn) is maintained in the range 0.5–5.0 and preferably 1–4. This ratio has a direct effect on the level of PFBA and DCF in the oxidizer effluent. It has been determined experimentally using the apparatus which is described in Examples 1 through 18 and is illustrated schematically in FIG. 2 that at a given acetic acid consumption (burn), the levels of PFBA and DCF pass through a minimum with respect to Co/Mn. With reference to FIG. 3, when typical Co/Mn values are plotted against PFBA concentration at four burn levels, it may be seen that the level of PFBA rapidly increases at ratios less than 0.5 for all levels of burn. Although the optimum Co/Mn can vary with the mechanics of the system, i.e., the scale of operation, oxidations conducted outside of the aforementioned range restrict the conditions under which acid of acceptable purity can be obtained at economical rates and in many cases can result in unacceptably high levels of PFBA and DCF in the terephthalic acid, high burn, unacceptable economics or a combination of the foregoing.

Figure 4:
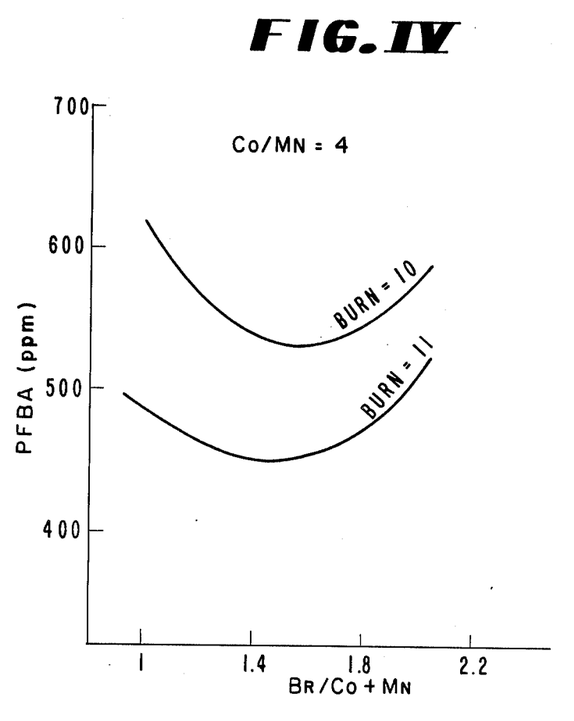

Bromine and sodium ions are critical components of the catalyst. The level of bromine is conveniently expressed as the mole ratio of bromine to the sum of the mols of cobalt plus manganese (Br/Co+Mn). This ratio must be maintained in the range of 0.8 to 3.0 and preferably 1.0 to 1.6. The Br/Co+Mn directly affects the level of PFBA in the terephthalic acid. There is an optimum ratio of bromine to metals at a given burn. FIG. 4 illustrates this effect at burn levels of 10 and 11 as determined on the apparatus discussed above. The results plotted therein show that the consumption of acetic acid (burn) markedly increases for a given level of PFBA outside of the optimum Br/Co+Mn ratio.

Some sodium must be present during the oxidation to minimize the corrosion of equipment which corrosion becomes excessive when sodium is eliminated from the system.

The sodium level is conveniently expressed as the mole ratio of sodium to the mols of cobalt plus manganese (Na/Co+Mn). This ratio is maintained in the range of 0.06 to 2.0 and preferably in the range 0.06 to 1.5. In general, the lower the amount of sodium in a given system, the lower the amount of acetic acid which must be consumed to achieve a given level of PFBA. However, in the absence of sodium, the corrosion of the equipment increases with the result that the polymer made from the terephthalic acid produced in such a system increases in color which is undesirable and is due to the effects of corrosion products in the acid.

The paraxylene fed to the oxidizer must be diluted with solvent. The solvent is a lower monocarboxylic acid having 2-8 carbon atoms, e.g., acetic acid singly or in combination with water. The amount of water, principally from recycle, is usually less than 10% by weight based upon the total weight of the mixture of paraxylene and solvent. This dilution is conveniently expressed in the weight ratio of solvent to paraxylene and is maintained in the range of 2.7 to 5.3.

The ratio of solvent (monocarboxylic acid plus water) to terephthalic acid is another important variable in the present invention. Increasing the ratio of solvent to terephthalic acid reduces the amount of acetic acid consumed (burned) at a given level of PFBA. However, increased amounts of solvent reduce the productivity of the system at a given hold-up time and require more expense for solvent recovery. Thus, it is necessary to operate the present process at a solvent to terephthalic acid weight ratio less than 3.0 and usually in the range 1.6-3.0 to obtain acid of satisfactory purity at optimum economics. While the upper limit of the amount of solvent relative to the acid is dictated by economic considerations the lower limit is dictated by the increasing difficulties encountered by handling of a concentrated slurry of acid, e.g., plugging of equipment etc.

The hold-up time of the contents in the oxidizer is another important variable. Although the level of PFBA in the terephthalic acid at a specific burn and solvent ratio is reduced with increasing hold-up time, the productivity of the system decreases. In order to produce terephthalic acid of acceptable purity at an acceptable rate, the hold-up time must be controlled within the range of of 33-80 minutes at the solvent ratios discussed herein.

The water content of the oxidation mixture is maintained in the range of about 5-17 and preferably 9-13% by weight based on the weight of liquid portion of the reaction mixture. It has been determined that the PFBA level at a given acetic acid consumption increases with increasing amounts of water thereby requiring more severe oxidation conditions for equivalent product quality, but the improved performance achieved by markedly reducing the amount of water is offset by increased distillation costs associated with higher volumes of water draw off. A balance between economical operation and production of a product of satisfactory purity dictates operation within the above range.

Another important variable is the oxygen content of the oxidizer off-gas and this must be maintained at from 3 to 6% by volume based upon the noncondensable portion of the off-gas from the oxidizer. Several by-products of the oxidation including highly colored 2,6-dicarboxyfluorenone (DCF) affect the color of the terephthalic acid and/or the polymer produced therefrom. The level of these impurities, especially DCF, rises sharply as the oxygen content of the off-gas decreases. When the oxygen content of the oxidizer off-gas is reduced to 2.5% the level of DCF increases to about 34 parts per million and the TPA "b" increases to about 5. This clearly demonstrates the need for the maintenance of at least 3 and preferably 4 to 6% total oxygen in the oxidizer off-gas. As would be apparent to one skilled in the art, the upper limit of oxygen is dictated by the need to operate safely below the explosive limits for the off-gas composition.

Operation within the aforementioned ranges will not assure the production of terephthalic acid of satisfactory purity and at satisfactory rates. The art recognizes that some acetic acid is consumed during the oxidation and that this consumption represents an economic penalty but it has now been discovered that a certain amount of acetic acid must be consumed to obtain a satisfactory product and that the productivity of the system must be maintained within limits to provide economic operation. A convenient method for monitoring the acetic acid consumption is the burn of acetic to carbon oxides. Although the total consumption of acetic acid is not measured by burn because acetic acid is consumed in other reactions, e.g., by the formation of methyl acetate and methyl bromide etc., these other reactions are in relatively constant proportion to burn in a given system and, therefore, burn will reflect the total consumption of acetic acid. Accordingly, two additional constraints upon the general conditions set forth hereinabove must be observed in order to produce fiber-grade terephthalic acid at acceptable rates. These are burn number and productivity which variables must be maintained in the range 8.0-15 and 0.45-1.45, respectively. Burn or burn number is defined as the pounds of acetic acid equivalent to carbon monoxide plus carbon dioxide in the oxidizer off-gas per 100 lbs. of terephthalic acid produced wherein acetic acid is taken as the source of substantially all the carbon oxides in the off gas. In a continuous process the relationship of burn to the process variables is set forth in the following equation:

$$\text{Burn} = \frac{k_1 (HUT)^{0.88} (CAT) e^{(0.044 \, T^\circ C. \, - \, 0.026 \, H_2O)}}{(SR)^{0.44}}$$

wherein the constants $k_1$ and $k_2$ and the variables $X_1$, $X_2$, $X_3$, hold-up time (HUT), catalyst concentrations (CAT), solvent ratio (SR) are defined as follows:

$k_1 = k_2[0.3762 + 0.4952 \ln(X_1) + 0.4146\sqrt{X_2} + 2.594 X_3 - 1.866 X_3^2]$ $k_2$ = system constant
$X_1$ = Br/(Co+Mn) mole ratio
$X_2$ = Na/Br mole ratio
$X_3$ = Co/(Co+Mn) mole ratio
HUT = Hold-up time, minutes (i.e., lbs. material in oxidizer divided by lbs. effluent/minute leaving the oxidizer)
CAT = 1000 × (Moles Co+Mn/mole p-xylene)
SR = lbs. solvent ($H_2O$ + HOAc)/lbs terephthalic acid in effluent from oxidizer
T = °Centigrade
$H_2O$ = weight % $H_2O$ in the liquid portion of oxidation mixture The system constant, $k_2$, is dependent upon characteristics other than the variables discussed hereinabove, e.g., equipment design and precision of operation, etc. but is readily determined for a given system. The average system constant ($k_2$) for the small scale operation set forth in Examples 1–18 was $81 \pm 5.2 \times 10^{-7}$ (two standard deviations) and the $k_2$ for the larger scale operation set forth in Examples 19–33 was $66 \pm 4.0 \times 10^{-7}$ with an average value of $73 \pm 13 \times 10^{-7}$. Since the burn predicted by the above equation is proportional to $k_2$, the system constant is determined by comparing the measured burn determined from the carbon oxides in the off-gas with the burn predicted by the above equation and adjusting $k_2$ so that the measured burn and the predicted burn coincide. For example, if $k_2$ is initially selected as $73 \times 10^{-7}$ the actual $k_2$ for a given system is determined by the following equation $$k_2 = \frac{\text{measured burn}}{\text{predicted burn (from equation)}} \times 73 \times 10^{-7}$$

As discussed above, the productivity must be maintained between 0.45 and 1.45 pounds of terephthalic acid per minute per one hundred pounds of reactor contents. Productivity is defined by the following equation:

$$\text{Productivity} = \frac{100}{(HUT)(1 + SR)} \text{ pounds per minute per one hundred pounds of reactor content}$$

wherein "HUT" and "SR" are defined as above.

In addition to the requirements that the present process be conducted within the general range of conditions hereinabove discussed, the variables $X_2$, $X_3$, CAT and SR can also be assigned ranges for optimum operation. The mole ratio of sodium to bromine ($X_2$) is maintained in the range 0.05–1.5 and preferably in the range 0.05–1.0. The mole ratio of cobalt to the total mols of cobalt plus manganese ($X_3$) is maintained in the range 0.33–0.83. The concentration of catalyst (CAT), i.e., 1000 times the mols of cobalt plus manganese per mol of paraxylene is maintained in the range 2.0–8.0 while the solvent ratio (SR) is maintained at less than 3 and preferably in the range of 1.6–3.0.

If it is desired to operate with burn at or near the minimum, e.g., 8.0–8.5 then the Co/Mn should be maintained in the range 0.5–2.2 and the Na/Co+Mn should be maintained at less than 0.5 for satisfactory results.

In the practice of the present invention the slurry from the oxidizer is subjected to a post treatment which further reduces the undesirable impurities in both the terephthalic acid and the mother liquor. Several post-treatments can be employed, e.g., digestion, but it is preferred to direct the effluent from the principal oxidizer to a second oxidizer wherein the slurry is subject to milder oxidation conditions as compared to the initial oxidation at a temperature of up to 40° C. and preferably 5°–30° C. lower than that employed during the principal oxidation while the mixture is contacted with air or a gas having a reduced oxygen content compared to the gas in the principal oxidizer, i.e., the oxygen level of the off gas on a noncondensable basis is in the range of 1 to 8% and preferably in the range of 3–5% oxygen before the terephthalic acid is discharged and separated from the mother liquor. This preferred treatment is described in more detail in the Examples.

The foregoing post treatment processes can also be combined. A preferred combination involves the post oxidation followed by digestion.

Usual considerations obvious to one skilled in this art of oxidation, i.e., the use of corrosion resistant materials of construction to minimize the deterioration of equipment and contamination of the product need not be discussed in detail.

The following examples are presented to illustrate but not to restrict the present invention. Parts and percentages are by weight unless otherwise noted. The TPA "b" color reported in Examples 1–18 in some cases exceeds the maximum value of 2.0 as discussed herein above. However, the PFBA and DCF levels indicate that the terephthalic acid is polymer grade and the interaction of the process variables, i.e., the burn and solvent ratio relationships are as set forth above. The high TPA "b" color is believed to be caused by contamination of the acid due to the scale of operation, e.g., the exposure of the terephthalic acid to possible sources of contamination during recovery of the acid. Operation at a larger scale as shown in Examples 19–33 reduces the contamination because the product is exposed to fewer sources thereof. Except as noted, the results are otherwise comparable.

EXAMPLE 1

Figure 2:
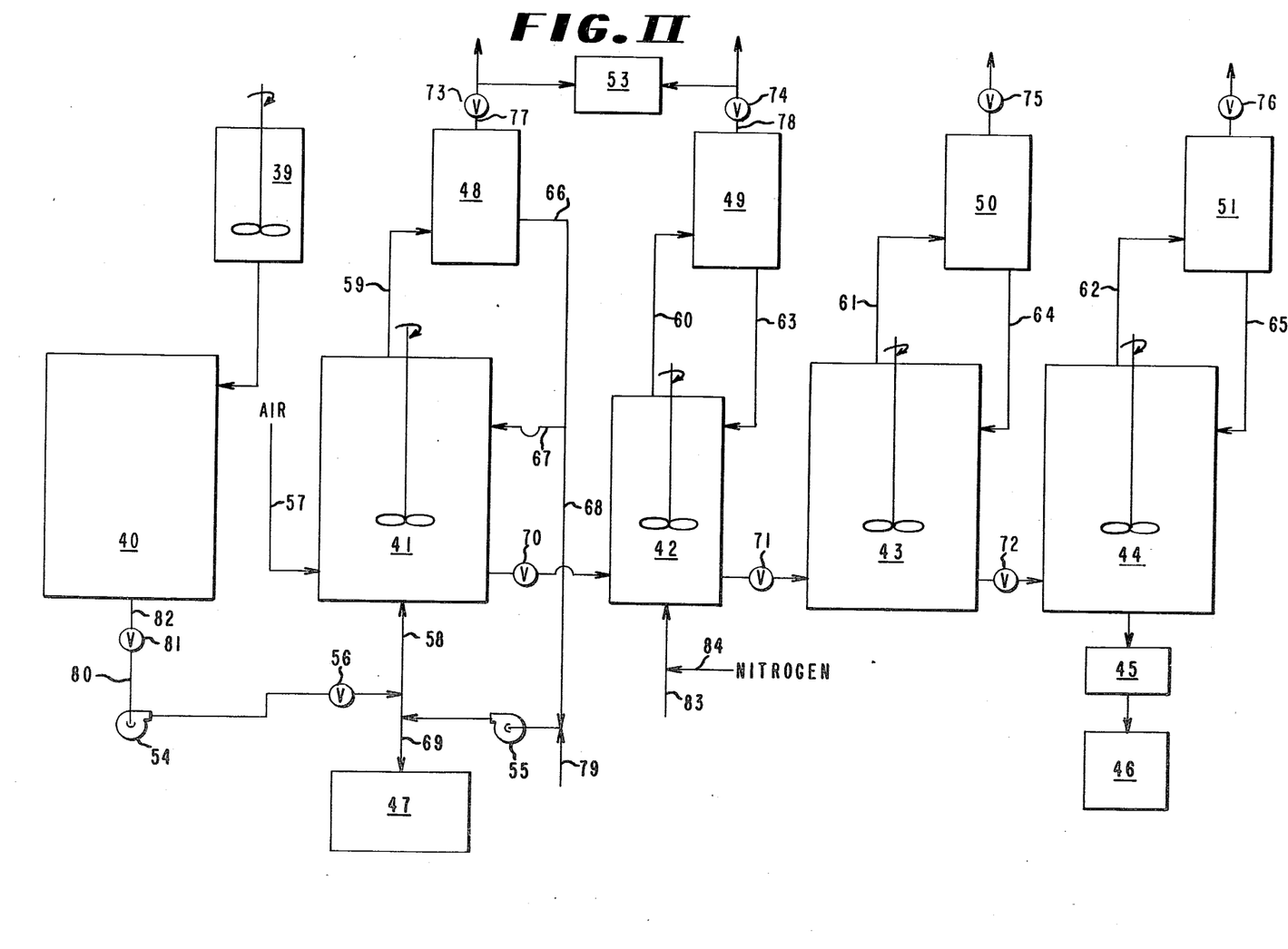
Figure 3:
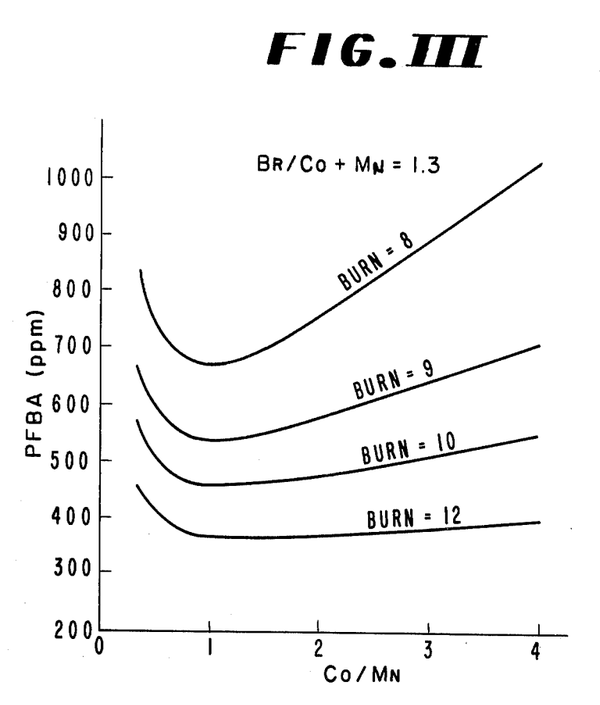
FIGS. 3 and 4 are graphs illustrating the relationship between the PFBA content and catalyst composition.

The apparatus employed in this example is schematically illustrated in FIG. 2 accompanying this application. The principal equipment equipment pieces are a feed tank 40, oxidizing autoclaves 41 and 42, stirred autoclaves 43 and 44, filter 45, product tank 46, purge receiver 47, reflux condensers 48, 49, 50 and 51, gas chromatographs 53 and constant displacement pumps 54 and 55. All agitators for the autoclaves are driven by suitable laboratory scale driving mechanisms. The tank 40 of approximately 18.9 liters (5 gal) volume is constructed of 316 stainless steel. The autoclaves, reflux condensers and all lines carrying products are constructed of corrosion resistant titanium. Feed is removed from tank 40 by a constant displacement pump 54. The rate of feed is also controlled by automatic valve 56 in a conventional manner. Acetic acid, paraxylene, water and catalyst ingredients are mixed in preselected proportions in agitated tank 39 to provide a uniform solution for several hours operation and introduced into tank 40 as required. Metered air is introduced via line 57 into autoclave 41. The agitator in autoclave 41 is provided in the upper portion with four down-pitch blades and in the lower portion with four flat impeller type blades. Autoclaves 41, 43 and 44 are of standard design having a volume of 2 gallons (7.6 liters) and are agitated. Autoclave 42 has a volume of approximately one gallon (3.8 liters). All autoclaves are electrically heated. The liquid level in autoclaves 41 and 42 is maintained at approximately 75% of this volume and the liquid level in autoclaves 43 and 44 is maintained at approximately 65% of this volume all by electroconductivity probes. The off-gas from autoclaves 41, 42, 43 and 44 is directed via lines 59, 60, 61 and 62, respectively, to off-gas condensers 48, 49, 50 and 51 where the condensables are removed and returned to autoclaves 42, 43 and 44 via lines 63, 64 and 65, respectively. A portion of the condensate in line 66 is returned to the upper part of autoclave 41 via line 67 with the remainder being directed via line 68 to pump 55 for return to the lower part of autoclave 41 via line 58 or to purge receiver 47 via line 69. The flow between the autoclaves is controlled by automatic valves 70, 71 and 72. The pressure in autoclaves 41 through 44 is controlled by restricting the flow of off-gas using valves 73, 74, 75, and 76, respectively. The concentration of oxygen, carbon dioxide, carbon monoxide and other by-products in the off-gas (lines 77 and 78) is monitored by gas chromatographs 53. The gas venting from the reflux condensers can be directed to a suitable recovery apparatus.

A feed mix was formulated by combining the following:

| | |
|---|---|
| Glacial acetic acid | 241.2 lbs. |
| p-xylene | 52.7 lbs. |
| Water | 5000 gm. |
| $Co(C_2H_3O_2)_2 \cdot 4H_2O$ | 117.8 gm. |
| $Mn(C_2H_3O_2)_2 \cdot 4H_2O$ | 38.6 gm. |
| NaBr | 38.9 gm. |
| 48% acqueous HBr soln. | 106.3 gm. | and charging the mixture as needed to feed tank 40.

A flow of 90% aqueous solution of acetic acid was established through the unit by introducing the acid at the intake of pump 55, via line 79 and to autoclave 41 via line 58. After establishing a level of approximately 75% of the volume in autoclave 41 the control valve 70 was opened and autoclaves 42, 43 and 44 were permitted to fill in sequence to the levels indicated above. After the flow of acetic acid was established through the autoclaves, the vessels were heated to the following temperatures.

| Autoclave No. | Temperature °C. |
|---|---|
| 41 | 215 |
| 42 | 191 |
| 43 | 155 |
| 44 | 88 |

After the autoclaves had reached the indicated temperatures an initial charge of catalyst solution was prepared by combining the following compounds and was injected into autoclave 41 via line 80 using feed pump No. 54.

400 ml acetic acid
90 ml $H_2O$
5.25 gm. $Co(C_2H_3O_2)_2 \cdot 4H_2O$
1.72 gm. $Mn(C_2H_3O_2)_2 \cdot 4H_2O$
1.74 gm. NaBr
4.74 gm. 48% aqueous HBr The feed mixture was isolated from the system during the injection of the initial catalyst charge. After the injection of the initial charge of catalyst was completed, the flows of feed mix (line 82), air (lines 57 and 83) and nitrogen (line 84) were started and the apparatus was lined out according to the following conditions.

| | |
|---|---|
| Feed (Line 82) | 82 grams/minute |
| Recycle (Line 68) | 84.1 grams/minute |
| Purge (Line 69) | 28 grams/minute |
| Air (Line 57) | 2.08 SCFM |
| (Line 83) | 0.088 SCFM |
| Nitrogen (Line 84) | 0.167 SCFM |

The diluted air fed to autoclave 42 contained 7.2% oxygen. Vent valves 74, 75 and 76 were then manually set to obtain the following pressures in the autoclaves. Vent valve 73 is set to maintain at temperature of 215° C. in autoclave 41 (276 psig).

| Autoclave No. | Pressure Psig |
|---|---|
| 42 | 202 |
| 43 | 46.6 |
| 44 | Atmospheric |

The system was operated for 9 hours at the above conditions. The main oxidizer off-gas (line 77) averaged 5.7 mole percent $O_2$, 2.06 percent $CO_2$, and 0.56% CO during the steady portion of the operation. The off-gas from autoclave 42 (line 78) contained 4.0 oxygen for the same period. The purge (line 69, purge receiver 47) functioned as a water draw-off. The water and methyl acetate content of the purge was continuously monitored by gas chromatography. The purge contained bromine species at an average of 52 ppm calculated as bromine, 18.2% water, 0.54% methyl acetate, 0.034% methanol and 81.2% acetic acid. The draw-off of product slurry (line 70) from autoclave 41 averaged 3800 gm/hr. The slurry was drained from autoclave 44 at 1 hour intervals and weighed (average 3800 gm). During the eighth and nineth hours of operation, the slurry was directed to a coarse glass filter (item 45) wherein the terephthalic acid is separated from the mother liquor. The weight of the mother liquor was noted and was submitted for analysis for water (10.7%) and PFBA (222 ppm). Approximately 1128 grams (average) of terephthalic acid on a dry basis was obtained during several hours of operation amounting to a yield of 92.0 based upon paraxylene. After the terephthalic acid which had been collected was thoroughly washed with 500 gms of 95% acetic acid and dried with hot nitrogen at 90° C., a 500 ml portion thereof was reslurried with 750 ml of 95% acetic acid at 90° C. This resultant slurry was filtered to recover the terephthalic acid and the washed acid was dried under nitrogen and submitted for analysis. The variables in the burn and productivity equations are determined by calculation from the flow rate feed and product compositions, etc. and are set forth in Table I. The value of $k_2$ was $87 \times 10^{-7}$. The level of PFBA and DCF is determined by gas chromatography on a Perkin Elmer Model 900 equipped with a flame ionization detector. PFBA is measured by injecting a solution of the acid in bis-trimethylsilylacetamide into a $\frac{1}{8}" \times 8'$ column in 10% SE-30 on "Anakrom" ABS 70–80 mesh with the injection port held at 280° C., the manifold at 300° C., the helium flow at 60 cc/min and the temperature program 80°–290° C. at 8° C. per minute. The PFBA from a silylated sample elutes in about 12 minutes and terephthalic acid about 17 minutes. The level of DCF is determined by esterifying a sample of terephthalic acid in methanol containing 20% aqueous HCl dissolved therein. The cooled sample is filtered and then toluene followed by water are added. The toluene layer is then injected into $\frac{1}{4}" \times 6'$ column in 10% OV-101 on "Chromosorb" WHP with the injection port and detector at 300° C. and the helium flow at 60 cc/min. The elution time for DCF is approximately 18 minutes.

EXAMPLES 2–4

The general procedure of Example 1 was repeated under the conditions set forth in Table II. The results are reported in Table I.

EXAMPLE 5

The general procedure of Example 1 was repeated except that the level of sodium and bromine was increased by increasing the sodium bromide in the catalyst feed. The results are reported in Table I.

EXAMPLES 6–8

The general procedure of Example 1 was repeated except that the solvent ratio (SR) was varied by changing the solvent to paraxylene in the feed. The results are reported in Table I.

EXAMPLES 9–11

The general procedure of Example 1 was repeated except that the hold-up time was varied by changing the feed rate. Comparative A shows that when the hold-up time is increased beyond the ranges specified herein, the productivity of the system decreases to an undesirable level. The results are reported in Table I.

EXAMPLES 12–14

The general procedure of Example 1 was repeated except that the amount of water in the oxidation was varied as indicated by varying the amount of draw-off (line 69). The results are reported in Table I. Example 7 also demonstrates the range of water in the system.

EXAMPLES 15–16

The general procedure of Example 1 was repeated except that the temperature was maintained at 211° C. and 223° C. The results are reported in Table I.

EXAMPLES 17–18

The general procedure of Example 1 is repeated except that the system is operated at the lower limit of the burn requirements. In order to achieve satisfactory results the Co/Mn and the sodium level must be closely controlled. The results are reported in Table I.

The following Examples are presented to illustrate the practice of the present invention on a larger scale than the foregoing Examples. The TPA "b" color (as well as the PFBA and DCF levels) for the acid produced in this larger scale equipment is within the limits as described above.

EXAMPLE 19

With reference to FIG. 1 and the description thereof hereinabove, the mixture to be oxidized is prepared by introducing into mix tank 1 catalyst and promoter (line 2) at a rate of 0.850 parts/hr., p-xylene (line 3) at 29 parts/hr and 96% acetic acid (line 4) (balance essentially water) at 108.8 parts/hr. The catalyst and promoter are introduced as a solution containing cobalt acetate tetrahydrate, manganese acetate tetrahydrate, sodium bromide, 48% hydrogen bromide and water. Of the total bromine, 29% is introduced as NaBr and 71% as HBr. The oxidation charge is thoroughly mixed in tank 1 and by analysis contains 19.9% p-xylene, 75.6% acetic acid, 4.4% water, 292 ppm Co, 68 ppm Mn, 705 ppm Br and 108 ppm Na. The charge is introduced into oxidizer 5 via line 6 at a rate of 66.2 parts/hr and air is introduced via line 7 at 87 parts/hr. The oxidizer 5 is maintained at about 218° C. by control of the pressure at about 325 psig. The oxidizer off-gas is directed to condensers 9 and 10. One portion of reflux (line 12) is returned at a rate of 23 parts/hr. Another portion is returned via line 14 at a rate of 209 parts/hr while the third portion is removed from the system via line 13 at a rate of 17.6 parts/hr for recovery of desirable organics. The product is removed as a slurry via line 16 at a rate of 61.377 parts/hr and directed to oxidizer/crystallizer 17. The draw-off (line 13) and the water content in the feed (line 6) are selected and adjusted to maintain a water content in oxidizer 5 of 11.5% as measured in the slurry removed via line 16. The hold up time in oxidizer 5 is 63 minutes as measured by parts of material in the oxidizer divided by parts of effluent/minute leaving the oxidizer. The burn was 12.2. The air feed (line 7) is controlled to maintain an oxygen content in the noncondensables (line 15) of 5.0 volume percent. Oxidizer-crystallizer 17 is maintained at 199° C. and 150 psig. Air (line 7) at a rate of 0.9 parts/hr and off-gas return (line 22) at a rate of 2.63 parts/hr are mixed and directed to crystallizer 17 to maintain an oxygen content of 4.0 volume percent in the off-gas in line 24. Slurry is withdrawn from crystallizer 17 at a rate of 61.377 parts/hr via line 25 and is cooled and separated. Dried terephthalic acid is produced at a rate of 21.263 parts/hr and has the properties set forth in Table III. The $k_2$ was $64.1 \times 10^{-7}$.

EXAMPLES 20–32

Example 19 is repeated except that the feed composition of mix tank 1 and the flows are adjusted to give the values and results set forth in Table III. The average $k_2$ was $66 \pm 4.0 \times 10^{-7}$ (two standard deviations).

Table 1

| Example No | Co/Mn | Br/Co + Mn ($X_1$) | Na/Co + Mn | HUT (Min) | $H_2O$ (%) | Temp. (°C.) | CAT | SR |
|---|---|---|---|---|---|---|---|---|
| 1 | 3.0 | 1.6 | 0.6 | 55 | 10.7 | 215 | 2.80 | 2 |
| 2 | 0.5 | 1.3 | 0.3 | 55 | 10.6 | 215 | 3.81 | 2 |
| 3 | 1.0 | 1.5 | 0.5 | 55 | 8.9 | 215 | 3.02 | 2 |
| 4 | 5.0 | 1.5 | 0.5 | 55 | 11.0 | 215 | 3.22 | 2 |
| 5 | 3.0 | 1.9 | 0.9 | 55 | 9.4 | 215 | 2.80 | 2 |

Table 1-continued

| | | | | | | | | | |
|---|---|---|---|---|---|---|---|---|---|
| 6 | 3.0 | 1.3 | 0.3 | 55 | 11.9 | 215 | 4.53 | 1.7 | |
| 7 | 3.0 | 1.3 | 0.3 | 55 | 5.7 | 215 | 4.53 | 2.0 | |
| 8 | 3.0 | 1.3 | 0.3 | 55 | 12.0 | 215 | 4.53 | 3.0 | |
| 9 | 3.0 | 1.3 | 0.3 | 33 | 13.4 | 215 | 6.40 | 2 | |
| 10 | 3.0 | 1.3 | 0.3 | 55 | 13.6 | 215 | 3.75 | 2 | |
| * | 3.0 | 1.3 | 0.3 | 90 | 13.0 | 215 | 2.69 | 2 | |
| 11 | 3.0 | 1.3 | 0.3 | 33 | 12.4 | 215 | 6.11 | 2 | |
| 12 | 3.0 | 1.3 | 0.3 | 55 | 12.5 | 220 | 3.11 | 2 | |
| 13 | 3.0 | 1.3 | 0.3 | 55 | 7.1 | 220 | 2.6 | 2 | |
| 14 | 3.0 | 1.3 | 0.3 | 55 | 17.0 | 220 | 3.72 | 2 | |
| 15 | 2.0 | 1.5 | 0.5 | 55 | 10.2 | 211 | 3.0 | 2 | |
| 16 | 3.0 | 1.3 | 0.3 | 55 | 13.6 | 223 | 3.11 | 2 | |
| 17 | 1.0 | 1.2 | 0.3 | 55 | 10.1 | 214 | 3.1 | 2 | |
| 18 | 0.5 | 1.3 | 0.3 | 55 | 9.8 | 215 | 2.79 | 2 | |

| Example No | Na/Br ($X_2$) | Co + Mn ($X_3$) | CO Burn | Productivity | PFBA (ppm) | DCF (ppm) | TPA b | Off-gas $O_2$ (I) |
|---|---|---|---|---|---|---|---|---|
| 1 | .38 | .75 | 10.42 | .606 | 451 | 6.9 | 2.1 | 5.7 |
| 2 | .23 | .33 | 12.68 | .606 | 456 | 4.6 | 2.6 | 5.2 |
| 3 | .33 | .50 | 11.40 | .606 | 404 | 3.6 | 2.2 | 4.8 |
| 4 | .33 | .83 | 12.66 | .606 | 359 | 8.3 | 1.9 | 4.7 |
| 5 | .47 | .75 | 11.44 | .606 | 470 | 10.0 | 2.5 | 5.1 |
| 6 | .23 | .75 | 11.12 | .606 | 584 | 13.9 | 3.4 | 4.8 |
| 7 | .23 | .75 | 11.04 | .606 | 538 | 9.5 | 3.0 | 5.1 |
| 8 | .23 | .75 | 11.2 | .606 | 320 | 4.4 | 1.2 | 5 |
| 9 | .23 | .75 | 12.58 | 1.01 | 606 | 8.5 | 1.3 | 5.0 |
| 10 | .23 | .75 | 12.10 | .606 | 568 | 9.6 | 2.3 | 4.6 |
| * | .23 | .75 | 12.06 | .370 | 408 | 12.6 | 2.6 | 4.6 |
| 11 | .23 | .75 | 11.84 | 1.01 | 626 | 8.8 | 1.6 | 4.9 |
| 12 | .23 | .75 | 9.56 | .606 | 544 | 12.8 | 2.7 | 4.5 |
| 13 | .23 | .75 | 10.78 | .606 | 552 | 13.7 | 3.0 | 4.5 |
| 14 | .23 | .75 | 10.12 | .606 | 668 | 19.4 | 2.9 | 4.5 |
| 15 | .33 | .67 | 10.10 | .606 | 394 | 13.7 | 3.0 | 4.8 |
| 16 | .23 | .75 | 10.58 | .606 | 648 | 17.6 | 2.9 | 4.8 |
| 17 | .25 | .50 | 7.80 | .606 | 692 | 7.6 | 3.0 | 4.9 |
| 18 | .23 | .33 | 8.06 | .606 | 755 | 8.7 | 3.0 | 4.9 |

*Comparative

TABLE II

| | EXAMPLE NO. | | |
|---|---|---|---|
| | 2 Run 81976 | 3 Run 217B6 | 4 Run 20976 |
| Feed Mix (tank 40) | | | |
| Glacial acetic acid, lbs. | 80.4 | 80.0 | 241.0 |
| p-xylene lbs. | 17.6 | 17.6 | 52.7 |
| Water gm. | 1667 | 1666 | 5000 |
| $Co(C_2H_3O_2)_2 \cdot 4H_2O$ | 23.7 gm | 148 ppm (Co) | 150.2 gm |
| $Mn(C_2H_3O_2)_2 \cdot 4H_2O$ | 46.7 gm | 129 ppm (Mn) | 29.6 |
| NaBr | 8.8 gm | [ 563 ppm total bromine ] | 37.2 |
| 48% aqueous HBr soln. | 48.2 gm. | | 122 |
| Temperature, °C. | | | |
| Autoclave 41 | 215 | 215 | 215 |
| Autoclave 42 | 184 | 189 | 190 |
| Autoclave 43 | 155 | 156 | 154 |
| Autoclave 44 | 87 | 86 | 88 |
| Initial Charge Autoclave 41 | | | |
| Glacial Acetic Acid, ml | 400 | 400 | 400 |
| Water, ml | 90 | 90 | 90 |
| $Co(C_2H_3O_2)_2 \cdot 4H_2O$, gm | 3.17 | 3.77 | 6.76 |
| $Mn(C_2H_3O_2)_2 \cdot 4H_2O$, gm | 6.25 | 3.72 | 1.33 |
| NaBr, gm | 1.18 | 0.57 | 1.68 |
| 48% aqueous HBr soln., gm | 6.45 | 5.11 | 5.46 |
| Flow | | | |
| Feed (line 82), gm/min | 81.0 | 81.3 | 81.4 |
| Recycle (line 68), gm/min | 84.9 | 84.2 | 84.3 |
| Purge (line 69), gm/min | 28.0 | 28.0 | 27.8 |
| Air (line 57), SCFM | 2.15 | 2.14 | 2.42 |
| (line 83), SCFM | 0.086 | 0.079 | 0.081 |
| Nitrogen (line 84), SCFM | 0.143 | 0.145 | 0.145 |
| Diluted air to autoclave 42, % $O_2$ | 7.9 | 7.4 | 7.5 |
| Pressures | | | |
| Autoclave 41, psig | 307 | 308 | 312 |
| Autoclave 42, psig | 196 | 188 | 191 |
| Autoclave 43, psig | 47 | 48 | 47 |

TABLE II -continued

| | EXAMPLE NO. | | |
|---|---|---|---|
| | 2 Run 81976 | 3 Run 217B6 | 4 Run 20976 |
| Autoclave 44, psig | atmos. | atmos. | atmos. |
| Off-gas (line 77), % $O_2$ | 5.2 | 4.8 | 4.6 |
| % $CO_2$ | 2.76 | 2.66 | 2.87 |
| % CO | 0.77 | 0.71 | 0.83 |
| (line 78), % $O_2$ | 4.7 | 5.3 | 5.8 |
| Purge Receiver 47 | | | |
| Bromine, ppm | 64 | 54 | 85 |
| Water, % | 18.2 | 16.2 | 19.9 |
| Methyl acetate, % | 0.48 | 0.44 | 0.48 |
| Methanol, % | 0.04 | 0.02 | 0.017 |
| Acetic acid, % | 81.3 | 83.3 | 79.6 |
| Slurry draw-off (line 70), gm/hr | 3684 | 3695 | 3640 |
| terephthalic acid, dry basis, gm/hr | 1212 | 1161 | 1346 |
| Mother liquor | | | |
| Water, % | 10.6 | 8.85 | 11.0 |
| PFBA, ppm | 312 | 201 | 200 |

Table III

| Example No. | Co/Mn | Br/Co + Mn ($X_1$) | Na/Co + Mn | HUT (Min) | $H_2O$ (%) | Temp. (°C.) | CAT | SR |
|---|---|---|---|---|---|---|---|---|
| 19 | 4.0 | 1.45 | .77 | 63 | 11.5 | 218 | 3.313 | 1.7 |
| 20 | 4.0 | 1.36 | .66 | 64 | 11.8 | 217 | 2.845 | 1.7 |
| 21 | 3.0 | 1.3 | .04 | 64 | 11.3 | 217 | 2.862 | 1.7 |
| 22 | 3.0 | 1.3 | .04 | 64 | 12.0 | 218 | 3.749 | 1.7 |
| 23 | 3.0 | 1.3 | .05 | 64 | 13.7 | 219 | 3.748 | 1.7 |
| 24 | 3.0 | 1.4 | .05 | 67 | 14.0 | 216 | 4.259 | 1.7 |
| 25 | 4.0 | 1.4 | .46 | 63 | 12.6 | 217 | 3.482 | 1.7 |
| 26 | 1.0 | 1.25 | 0.43 | 62 | 10.8 | 217 | 4.0 | 1.7 |
| 27 | 1.0 | 1.35 | 0.50 | 62 | 10.2 | 217 | 2.777 | 1.7 |
| 28 | 4.0 | 1.4 | .47 | 63 | 11.7 | 217 | 2.970 | 1.7 |
| 29 | 2.0 | 1.32 | .61 | 60 | 13.0 | 217 | 3.40 | 1.8 |
| 30 | 2.0 | 1.08 | .08 | 60 | 12.7 | 217 | 3.15 | 1.9 |
| 31 | 2.0 | 1.32 | .50 | 60 | 12.7 | 217 | 2.49 | 1.6 |
| 32 | 5.0 | 1.79 | 2.14 | 72.4 | 13.5 | 217 | 2.854 | 1.7 |
| 33 | 4.0 | 1.22 | 0.04 | 59 | 12.0 | 219 | 3.92 | 1.7 |

| Example No | Na/Br ($X_2$) | CO Co + Mn ($X_3$) | Burn | Productivity | PFBA (ppm) | DCF (ppm) | TPA b | Off-gas $O_2$ (%) |
|---|---|---|---|---|---|---|---|---|
| 19 | .53 | .80 | 12.2 | .59 | 410 | 7 | 0.9 | 5.0 |
| 20 | .44 | .80 | 10.2 | .58 | 600 | 11 | 1.4 | 5.3 |
| 21 | .03 | .75 | 9.4 | .58 | 720 | 14 | 2.0 | 5.1 |
| 22 | .03 | .75 | 10.0 | .58 | 440 | 10 | 1.5 | 4.3 |
| 23 | .04 | .75 | 10.4 | .58 | 438 | 7 | 0.9 | 5.0 |
| 24 | .04 | .75 | 11.4 | .55 | 430 | 8 | 1.2 | 5.0 |
| 25 | .35 | .80 | 11.4 | .59 | 460 | 9 | 1.0 | 5.1 |
| 26 | .34 | .50 | 11.6 | .60 | 440 | 5 | 0.8 | 6.4 |
| 27 | .37 | .50 | 10.2 | .60 | 760 | 12 | 2.0 | 6.3 |
| 28 | .34 | .80 | 9.6 | .59 | 765 | 15 | 1.7 | 5.3 |
| 29 | .45 | .67 | 12.2 | .60 | 538 | 10 | 0.9 | 5.0 |
| 30 | .07 | .67 | 10.0 | .57 | 737 | 14 | 1.8 | 5.0 |
| 31 | .38 | .67 | 9.6 | .64 | 716 | 14 | 1.8 | 5.1 |
| 32 | 1.19 | .83 | 11.6 | .51 | 680 | 8 | 1.0 | 5.0 |
| 33 | 0.033 | 0.8 | 12.62 | 0.63 | 390 | 14.4 | — | 3.5 |

We claim:

1. In a process for the preparation of fiber-grade terephthalic acid comprising oxidizing paraxylene with a molecular oxygen containing gas in a reactor in the presence of a catalyst consisting essentially of cobalt, manganese, sodium and bromine and a solvent comprising a lower monocarboxylic acid wherein (1) the oxidation is conducted in the liquid phase, (2) a portion of the contents of the reactor is continuously vaporized, withdrawn from the reactor and at least a portion thereof condensed and returned to the reactor and (3) the product is continuously withdrawn and subjected to treatment after oxidation and before recovery of the terephthalic acid, the improvement comprising maintaining a high productivity of fiber-grade terephthalic acid by maintaining (a) the temperature of the contents of the reactor at at least 210° C., (b) the molecular oxygen content of the vapor withdrawn from the reactor in the range 3.0–6.0% by volume at least in part by controlling the molecular oxygen introduced into the reactor, (c) the water level of the contents of the reactor in the range 5.0–17% by weight based upon the weight of the liquid portion of the contents of the reactor by controlling the amount of condensed vapor returned to the reactor (d) the mole ratio of cobalt to manganese in the range 0.5–5.0 (e) the burn in the range 8–15 burn units and (f) the productivity of the reaction in the range 0.45–1.45 pounds of terephthalic acid per minute per one hundred pounds of reactor contents.

2. The process of claim 1 wherein the weight ratio of lower monocarboxylic acid to terephthalic acid in the reactor is less than 3.0.

3. The process of claim 1 wherein the lower carboxylic acid is acetic acid.

4. The process of claim 1 wherein the molar ratio of sodium to the mols of cobalt plus manganese is maintained in the range of about 0.06–2.0.

5. The process of claim 3 wherein the molar ratio of bromine to cobalt plus manganese is maintained in the range 0.8–3.0.

6. The process of claim 5 wherein the molar ratio of sodium to the mols of cobalt plus manganese is maintained in the range 0.06–2.0.

7. The process of claim 3 wherein
   (1) the weight ratio of acetic acid to terephthalic acid in the reactor is in the range 1.6–3.0
   (2) the molar ratio of sodium to the mols of cobalt plus manganese is in the range 0.06–1.5
   (3) the molar ratio of cobalt to manganese is in the range 1–4
   (4) the molar ratio of bromine to cobalt plus manganese is in the range 1.0–1.6
   (5) the temperature is in the range 215°–223° C.
   (6) the water level of the contents of the reactor is in the range 9–13%.

8. A process for oxidizing paraxylene to terephthalic acid in the liquid phase in an oxidation zone in using an acetic acid solvent and the presence of a catalyst consisting of species of cobalt, manganese, sodium and bromine which are soluble in said solvent which process comprises contacting said paraxylene with air, vaporizing, removing and condensing a portion of the solvent, returning a portion of the condensed solvent to the oxidation zone and continuously removing a slurry of terephthalic acid from said zone while maintaining the conditions in the following ranges
   (a) the temperature in the zone in the range 215°–223° C.
   (b) the molecular oxygen content of the off gas from the zone after removal of condensables in the range 3.0–6.0%
   (c) the water content in the zone of 9–13% by weight based upon the weight of the liquid contents of the zone
   (d) the molar ratio of cobalt to manganese in the zone in the range 1.0–4.0
   (e) the weight ratio of solvent to terephthalic acid leaving the zone in the range 1.6–3.0
   (f) the molar ratio of sodium to cobalt plus manganese in the zone in the range 0.06–1.5
   (g) the molar ratio of bromine to cobalt plus manganese in the feed to the zone in the range 1.0–1.6
   (h) the burn in the zone in the range 8.0–15 and
   (i) the productivity in the range 0.45–1.45 pounds of terephthalic acid per minute per one hundred pounds of material in the zone and thereafter contacting the terephthalic acid slurry under oxidizing conditions which are milder than the initial oxidation prior to recovering the terephthalic acid.

9. A process for the preparation of fiber-grade terephthalic acid comprising oxidizing paraxylene with a molecular oxygen containing gas in a reactor in the presence of a catalyst consisting essentially of cobalt, manganese, sodium and bromine and a solvent comprising a lower monocarboxylic acid wherein (1) the oxidation is conducted in the liquid phase, (2) a portion of the contents of the reactor is continuously vaporized, withdrawn from the reactor and at least a portion thereof condensed and returned to the reactor and (3) the product is continuously withdrawn and subjected to treatment after oxidation and before recovery of the terephthalic acid wherein the process variables are maintained in relationship according to the following formula $$\text{BURN} = \frac{k_1 \, (\text{HUT})^{0.88} \, (\text{CAT}) e^{(0.044 \, T° C. \, - \, 0.026 \, H_2O)}}{SR^{0.44}}$$

wherein
Burn = 8.0–15
$k_1 = k_2[0.3762 + 0.4952 \ln(X_1) + 0.4146\sqrt{X_2} + 2.594X_3 - 1.866X_3^2]$
$k_2 = 73 \pm 13 + 10^{-7}$
$X_1 = 0.8$–3.0 (Br/(Co+Mn) mole ratio)
$X_2 = 0.05$–1.5 (Na/Br mole ratio)
$X_3 = 0.33$–0.83 (Co/(Co+Mn) mole ratio)
HUT = hold-up time in minutes
CAT = 2.0–8.0 (1000×moles of Co+Mn/moles p-xylene)
T° C. = temperature in degrees centigrade
$H_2O$ = weight percent water in the liquid portion of the oxidation mixture
SR = pounds of solvent per pound of terephthalic acid from the oxidizer.

10. The process of claim 9 wherein the productivity is maintained in the range 0.45–1.45 as defined by the formula $$\text{productivity} = \frac{100}{(\text{HUT}) \, (1 + SR)}$$

* * * * *

UNITED STATES PATENT OFFICE
CERTIFICATE OF CORRECTION

PATENT NO. : 4,158,738
DATED : June 19, 1979
INVENTOR(S) : Leon S. Scott & Roy W. Sommers It is certified that error appears in the above—identified patent and that said Letters Patent are hereby corrected as shown below:

Claim 9, column 18, line 34, should read:

$k_2 = 73 \pm 13 \times 10^{-7}$

Signed and Sealed this

Thirteenth Day of November 1979

[SEAL]

Attest:

RUTH C. MASON
Attesting Officer

LUTRELLE F. PARKER
Acting Commissioner of Patents and Trademarks